United States Patent [19]

Graves et al.

[11] Patent Number: 5,275,161
[45] Date of Patent: Jan. 4, 1994

[54] METHOD OF AND APPARATUS FOR MEASURING SULFIDES WITHIN A PERIODONTAL POCKET

[75] Inventors: Bruce B. Graves, Ypsilanti; Howard Diamond, Ann Arbor, both of Mich.

[73] Assignee: Diamond General Development Corporation, Ann Arbor, Mich.

[21] Appl. No.: 848,086

[22] Filed: Mar. 9, 1992

[51] Int. Cl.$^5$ .............................................. A61B 5/00
[52] U.S. Cl. ..................................... 128/635; 128/734
[58] Field of Search ............... 128/635, 639, 642, 734, 128/637, 632, 639; 433/229; 204/403, 431

[56] References Cited

U.S. PATENT DOCUMENTS

| | | | |
|---|---|---|---|
| 4,334,540 | 6/1982 | Preti et al. | 128/630 |
| 4,713,164 | 12/1984 | Krietemeier et al. | 204/400 |
| 4,750,496 | 6/1988 | Reinhart et al. | 128/635 |
| 4,834,101 | 5/1989 | Collison et al. | 128/635 |
| 4,920,980 | 5/1990 | Jackowski | 128/786 |
| 5,022,396 | 6/1991 | Watanabe | 128/642 |
| 5,083,565 | 1/1992 | Parins | 128/642 |

FOREIGN PATENT DOCUMENTS 1279370 1/1991 Canada .

OTHER PUBLICATIONS

"Hydrogen Sulfide Production from Gingival Crevicular Fluid", M. C. Solis-Gaffar et al., J. Periodontal, 1980, pp. 603-606.

"The Possible Role of Hydrogen Sulfide in Human Periodontal Disease", Anthony A. Rizzo, Periodontics, 1967, vol. 5, No. 5, pp. 233-236.

"Hydrogen Sulfide and Periodontal Disease", Allen Horowitz and Lars Folke, Periodontal Abstract, 1972, vol. XX, No. 2, pp. 59-62.

"Oxygen Tension ($pO_2$) in Untreated Human Periodontal Pockets", G. R. Mettraux et al., J. Periodontics, 1983, vol. 55, No. 9, pp. 516-521.

Primary Examiner—Angela D. Sykes
Attorney, Agent, or Firm—Krass & Young

[57] ABSTRACT

A method of and apparatus for diagnosing the presence and extent of disease activity within a periodontal pocket. A dual electrode probe having a first, working silver electrode and a second, reference silver/silver chloride electrode is inserted into the pocket to take data measurements of the electrochemical potential between the electrodes while they are immersed in the fluid contained in the periodontal sulcus. The strength of the potential reflects the amount of sulfides within the sulcus fluid and reflects the presence and extent of disease therewithin.

11 Claims, 1 Drawing Sheet

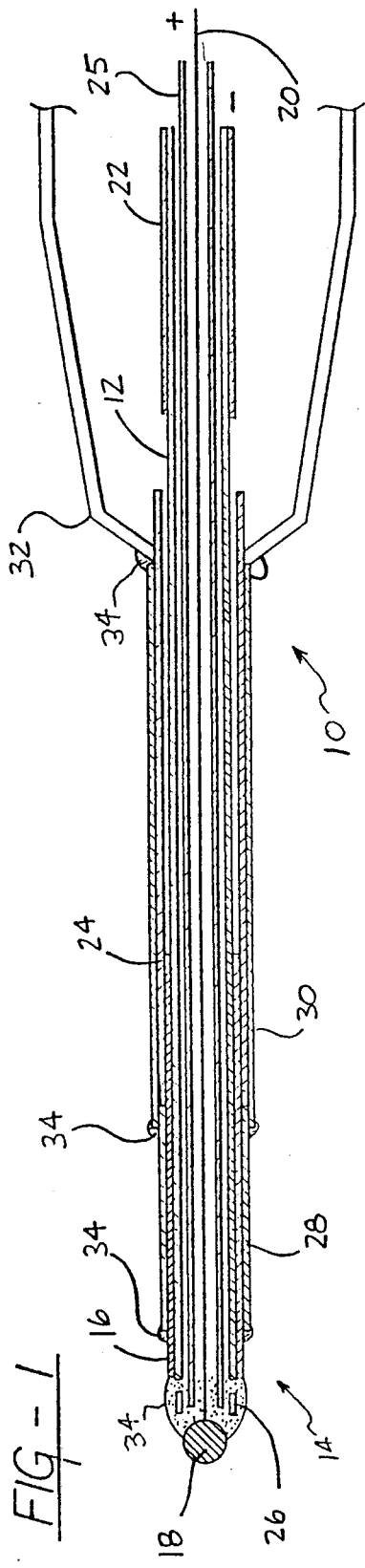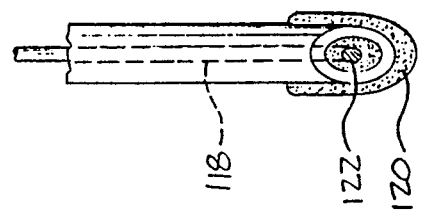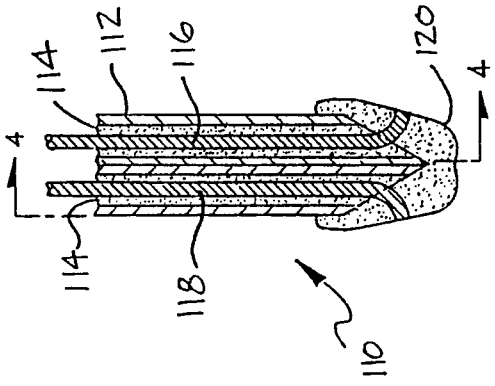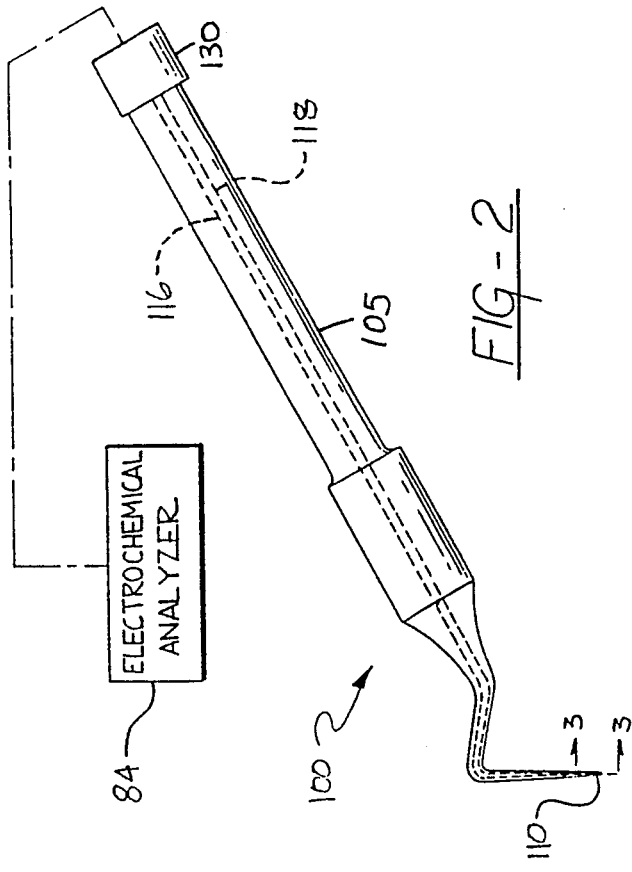

METHOD OF AND APPARATUS FOR MEASURING SULFIDES WITHIN A PERIODONTAL POCKET

This invention was made with government support under SBIR Grant# SSS-5(A) 1 R43 DE-09490-01 awarded by the National Institute of Dental Research, Public Health Service.

FIELD OF THE INVENTION

This invention generally relates to the field of detecting gingivitis and periodontal disease and, more particularly, to a method of and apparatus for measuring the concentration of sulfides within a periodontal pocket to determine the presence and extent of gingivitis and periodontal disease.

DESCRIPTION OF THE RELEVANT PRIOR ART

Gingivitis and periodontal diseases are, broadly speaking, diseases which causes inflammation of the gum area surrounding a tooth. They are thought to be caused by the activity of Gram-negative anaerobic organisms. Early symptoms include redness of the gingival margin surrounding the tooth, slight edema or slight retractability of this margin, and slight or delayed bleeding on probing of the margin. If left unchecked, gingivitis and periodontal disease may cause further and severe retraction of the gingival margin, continuous and/or spontaneous bleeding, and, even, eventual loss of the tooth due to the erosion of the supporting and investing structures surrounding the tooth, including the gums, cementum, periodontal membranes and alveolar bone, even though the tooth itself, may be perfectly healthy. It is thought that, in the United States each year, more teeth are lost to gingivitis and periodontal disease than to disease and decay within the tooth, itself.

Typically, the presence of gingivitis and periodontal disease enlarge the periodontal pocket or gingival sulcus of the affected tooth. The gingival sulci are the spaces or pockets between the gingival tissue (gums) and the teeth. Many experts in the field are of the belief that there is a correlation between the depth of a periodontal pocket and the severity of the disease. The depth of the periodontal pocket is usually measured from the margin or top of the gum to the epithelial attachment, the point where the gum attaches to the tooth. It is measured with a mechanical probe. However, other experts doubt the reliability of this correlation since the gingival margins of some patients may exhibit fairly deep pockets, and yet the patients have little or no active periodontal disease within said pockets. In some cases, disease may have been present in the past, but the organisms which cause the disease may no longer be present, or if present, active in the pocket.

From a treatment standpoint, it is important to know whether active periodontal disease is occurring within a periodontal pocket, and, if so, how severe the disease is. Hence, because even deep periodontal pockets do not necessarily correlate with the presence of active periodontal disease, merely measuring the depth of the pocket does not necessarily provide an accurate indicator of the necessity of treatment. Clearly, it would be desirable to find a more accurate means of determining the presence and extent of active periodontal disease.

It is known that the presence of active disease agents within the periodontal pocket results in measurable concentrations of hydrogen sulfide gas within said pocket. According to an article authored by M. C. Solis-Gaffar, K. N. Rustogi, and A. Gaffar, appearing in the *Journal of Periodontology*, October 1980, pages 603-606, there is a measurable relationship between gingival health, crevicular fluid flow and the production of hydrogen sulfide from the crevicular fluid. Furthermore, these authors observed a positive, moderate correlation between the degree of observed inflammation and the $H_2S$ generating potential of the gingival crevicular fluid. An even stronger correlation was found between the sulfide gases generated in the gingival crevicular fluid (GCF) and the volume of GCF within the pocket. According to Solis-Gaffar, et al., hydrogen sulfide concentration of around 8 nanograms of sulfur per 10 milliliters of GCF are typical of healthy gingiva, whereas concentration of above 40 are characteristic of severe gingivitis.

The method used by Solis-Gaffar, et al. for determining the hydrogen sulfide generating potential of gingival crevicular fluid involved a chromatographic method; sterile filter paper strips were inserted into the crevice to collect the GCF. The analytic method disclosed is complicated, involving a three-day incubation of the strips with an appropriate amino-acid, and subsequent analysis with gas chromatography and a flame photometric detection system. Obviously, while useful for experimental purposes, the method disclosed in the Solis-Gaffar, et al. paper is not practical in a clinical setting.

Other researchers have attempted to detect the presence of hydrogen sulfide by placing filter paper strips impregnated with lead acetate between the teeth and gums of patients suspected to be afflicted with periodontal disease. (See A. A. Rizzo, *Periodontics*, 5:233, 1967; and A. Horowitz and L. E. Fole, *Periodontal Abstracts*, 20:59, 1972.) Obviously, such methods are undesirable due to the known toxicity of lead. Additionally, such methods detect only the presence, not the concentration, of the sulfide gases and sulfide ions and particles in the sulcus fluid. Thus, with the above methods, quantitative measurements of the progress of periodontal disease cannot be made.

Other methods have been suggested for determining the presence of periodontal disease by either measuring the presence of certain components within the saliva or by probing the pocket with an electrochemical probe. For example, U.S. Pat. No. 4,334,540 to Preti broadly teaches a method for the detection of pyridines in mouth saliva. The reference teaches collecting saliva samples, incubating the samples, and collecting the volatiles from the saliva from the head space above the saliva. Again, this is an indirect method for making a gross determination of whether a patient has or is developing periodontal disease. U.S. Pat. No. 4,713,164 to Krietemeier discloses a method for analyzing malodors in the breath by means of a hand-held electrochemical detection means into which a sample gas stream is directed by blowing into the interior of the device. However, the reference does not teach anything about quantifying the presence or progression of periodontal disease, and does not teach how to make a hydrogen sulfide measurement around a specific tooth site. Also, it has been suggested by G. R. Mettraux, et al., *Journal of Periodontology*, 55:516–521 (1983) that an electrochemical sensor may be used to measure the concentration of oxygen in the sulcus of a tooth. Mettraux, et al., employ a $pO_2$ electrode which is inserted into the periodontal pocket. In this manner, the fluid in the periodontal pocket is measured to determine whether the subgingival environment is anaerobic or aerobic in nature. Finally, in Canadian Patent No. 1,279,370, an electrochemical sensor is inserted into the sulcus of the tooth to polarographically determine the ratio of at least two gases selected from the group consisting of oxygen, ammonia, hydrogen, methane, carbon dioxide and hydrogen sulfide in the crevicular fluid. The ratio measurements are correlated with known parameters to indicate the nature and presence or progression of periodontal disease.

None of the prior art teaches an effective method for directly measuring the concentration of sulfides or hydrogen sulfide in the gingival crevicular fluid. Clearly, it would be desirable to find a method for directly measuring such concentrations so that the presence and extent of periodontal disease may be immediately determined within the clinical setting.

SUMMARY OF THE INVENTION

The invention described and claimed herein is designed to overcome the shortcomings of the prior art noted above. In its broadest aspects, the invention is a method of and apparatus for detecting the presence and extent of disease within a periodontal pocket by direct measurement of the concentration of sulfides, including sulfide gases and sulfide ions and particles, within the GCF contained in the periodontal pocket. The method contemplates providing a dual electrode probe having a first silver, working electrode and a second silver/silver chloride, reference electrode which are electrically connected to an electrochemical analyzer (voltage indicator) capable of generating a data readout reflective of the strength of the electrical potential between the first and second electrodes. The probe is positioned within the periodontal pocket such that said electrodes are in contact with periodontal sulcus fluid contained therein to cause a potential between said first and second electrodes, the magnitude of said potential corresponding to the concentration of sulfides in said fluid. The electrochemical analyzer will then within a few seconds display a data readout which is indicative of the concentration of sulfides within the pocket. The dual electrode probe is removed from the periodontal pocket, and the data readout is compared with a predetermined standard to determine the presence and extent of periodontal disease.

The method further contemplates obtaining a baseline reading reflective of the potential difference between the first and second electrode by immersing the dual electrode probe within a test saline solution and recording the data readout generated by the analyzer prior to placing the probe within the periodontal pocket. A healthy pocket will, typically, achieve a data readout which differs little or not at all above the baseline readout, while a diseased pocket will give a much higher reading. Also, the test saline solution also serves as a cleaning solution for the probe tip to normalize the apparatus to the baseline between successive pocket readings on a given patient, especially in conjunction with electronic depolarization.

In the method claimed herein, the silver/silver chloride second electrode acts as a reference and is in equilibrium with the solution. Electrochemical action causes the pure silver first electrode to gradually become coated with a sulfide coating from the sulfide ion characteristic of periodontal disease. This process generates a potential with respect to the reference electrode that can be measured and is a function of the concentration of sulfide in the sulcus fluid. The electrochemical half cell reaction proceeds according to the equation:

Of course, a problem may arise because the silver chloride coating on the reference electrode will, in time, gradually become poisoned with sulfide, forming a silver sulfide surface. If the electrochemical reaction is allowed to proceed to equilibrium, both electrodes will be coated with silver sulfide and no electrical potential difference would be observed. However, the inventors of the present invention have surprisingly discovered that the process of converting the chloride coating on the reference electrode to sulfide takes a considerable amount of time to proceed to equilibrium. Before equilibrium is achieved, the process generates a voltage that is a function of the concentration of sulfide gases in the electrolytic solution. In fact, the apparatus gives a very rapid response in the clinical setting, and the typical probe response is on the order of a second or two. Some poisoning of the silver chloride coating of the reference electrode may occur due to sulfide contamination. However, the probe of the present invention may easily be fabricated as a disposable device, thus obviating this problem.

Also described and claimed herein is a dual electrode probe suitable for diagnosing the presence and extent of disease in a periodontal pocket by measuring the concentration of sulfide gases therein. The probe comprises a housing having a length and diameter suitably configured to be easily handled and manipulated in the mouth of a patient. A tip suitably configured to probe a periodontal pocket is disposed at a first end of the housing. The probe further comprises a pair of electrodes including a first silver, working electrode and a second silver, reference electrode having a silver chloride coating deposited thereon. Each of the pair of electrodes has a surface portion at least partially exposed in the tip and an interior portion disposed interior of said handle. The first and second electrodes are connected to, respectively, first and second electrical leads for placing the first and second electrodes in electrical communication with an electrochemical analyzer.

In a first embodiment of the probe of the present invention, the housing comprises a suitable length of double bore, bifilar, polymeric tubing. Each of said first and second electrodes is formed of a suitable length of silver wire extending through a bore of said bifilar tubing. A portion of each silver wire is left exposed at the tip of the probe, with the exposed portion of the reference electrode having a chloride coating deposited thereon. A potting material such as epoxy is disposed in both bores of the bifilar tubing to surround and support the pair of silver wires. The probe may further comprise means for stiffening each bore of the bifilar polymeric tubing, such as a length of tungsten wire which is disposed in each bore and is electrically insulated from the silver wire.

In a second embodiment, the probe of the present invention may comprise a housing formed of a suitable length of metal tubing, such as stainless steel hypodermic tubing. The first electrode comprises a layer of silver plated onto portions of the tubing, and the second electrode comprises a chloride coated silver ball disposed outside of the housing to form the tip of the probe. A suitable gage of polymeric tubing encloses and surrounds the metal housing, with a portion of the silver layer remaining exposed and uncovered by the polymeric tubing at the tip of the probe. A silver wire is attached to the chloride coated silver ball to form the second lead, and the first lead may be formed from the silver layer, first electrode itself. This embodiment is relatively easily fabricated from inexpensive materials. Hence, it may be provided as a disposable item. After readings from all of the tooth sites for a single patient have been taken, the probe is disposed of in an appropriate manner and a fresh probe used for the next patient.

BRIEF DESCRIPTION OF THE DRAWINGS

The following detailed description may best be understood by reference to the following figures in which:

FIG. 1 is a cross-sectional view of one embodiment of the dual electrode probe of the present invention;

FIG. 2 is perspective view of another embodiment of the probe of the present invention;

FIG. 3 is a detail view of the tip of the probe shown in FIG. 2; and

FIG. 4 is a 90° rotated view of the tip shown in FIG. 3.

DETAILED DESCRIPTION OF THE PREFERRED EMBODIMENTS

Throughout the following detailed description, like reference numerals are used to refer to the same element of the invention shown in multiple figures thereof.

Referring now to the drawing, and in particular to FIG. 1, there is shown a dual electrode periodontal probe 10 suitable for detecting the presence and extent of disease within the periodontal pocket. The probe 10 comprises a housing 12 in the form of stainless steel hypodermic tubing which has a tip 14 formed at one end thereof. A pair of electrodes including a first silver electrode 16 and a second, reference silver electrode 18 having a silver chloride coating deposited thereon are disposed in said tip 14, each of said pair of electrodes 16, 18 having a surface portion at least partially exposed in said tip 14, and an interior portion disposed interior of said housing 12.

In the embodiment shown in FIG. 1, the first electrode 16 is formed by regions of silver plated onto the stainless steel housing 12. Reference electrode 18 is formed by a ball of silver having a chloride coating formed thereon. The first and second electrodes 16,18, are in electrical communication with, respectively, first and second electrical leads 22, 20. First electrical lead 22 is formed by portions of the region of silver plated onto housing 12. Second electrical lead 20 is in the form of a fine silver wire connected to second electrode 18, said silver wire extending down the length of housing 12 to emerge from the rear thereof.

Probe 10 includes further structures which, while not necessary to the practice of the present invention, function to support and electrically insulate the working elements of the probe 10. To that end, a second stainless steel tubing 24 encircles a portion of housing 12. Polyimide tubing 28 of suitable bore enclosing housing 12 is disposed therearound, leaving a portion of the silver plating plated thereon exposed at the tip 14 of the probe to form first electrode 16. Similarly, a suitable bore of polyimide tubing 30 surrounds and encloses stainless steel tubing 24. Also, second lead 20 may also be enclosed by polyimide tubing 25, and the tip 14 portion of housing 12 may be terminated by a polyimide tubing spacer 26. Needle hub 32, which permits probe 10 to be more easily grasped, is disposed proximate the rear of housing 12. The joints between the various metal and polyimide elements are appropriately sealed by epoxy sealing agent 34, resulting in a probe 10 which is electrically insulated at all portions thereof except for the first and second electrodes 14,16, and the first and second leads 22,20. Probe 10 may be placed in electrical communication with an electrochemical analyzer (not shown) by plugging the rear of housing 12 into a conventional coaxial connector.

An alternate embodiment 100 of the probe of the present invention is shown in FIG. 2. Probe 100 comprises a housing 105 suitably configured to be easily handled and manipulated in the mouth of a patient. Probe 100 further includes tip 110, shown in greater detail in FIGS. 3 and 4. Tip 110 is formed of a suitable length of double bore, bifilar, poly-imide tubing 112, having two bores 114 extending therethrough. Disposed in bores 114 are first and second electrodes 116,118 which are formed of suitable lengths of 0.010 inch silver wire. The tip 110 further includes epoxy sealant 120 which encloses the end of the bifilar tubing 112. As can be seen most clearly in FIG. 4, which is a 90° rotation of the view shown in FIG. 3, a portion of the epoxy 120 is removed to leave an exposed surface 122 of electrode 118. Although not visible in FIG. 4, electrode 116 is treated in a similar manner to leave an exposed portion. The exposed portion 122 of silver wire second electrode 118 has a layer of chloride deposited thereon. Thus, the first electrode 116 serves as the working electrode of the probe 110, and the second electrode 118 serves as the silver/silver-chloride reference electrode.

As can be most clearly seen in FIG. 4, silver wire first and second electrodes 116,118 (shown in phantom in FIG. 2), extend through the entire length of housing 105 and are in electrical communication with a conventional electrical connector 130. The probe 100 may then be electrically connected to a conventional electrochemical analyzer 84, shown schematically in FIG. 2.

The tip 110 of probe 100 further includes a potting material 124 disposed in both bores 114 of bifilar tubing 112. The potting material 124 serves to support the electrodes 116,118, and stiffen the tip 110 of probe 100 so it more effectively may be inserted into a periodontal pocket (not shown). The tip 110 may further comprise other structures (not shown) which serve to further stiffen the tip 110, such as, for example lengths of tungsten wire disposed outside of or in each bore 114 of bifilar tubing 112.

Two embodiments of the probe of the present invention have been described in detail. However, it is to be understood that one skilled in the art of periodontal probe design may, by using the teachings of the present invention design a wide variety of probes which embody the inventive concepts claimed herein. For example, instead of the cylindrical shape depicted in the figures, the probe could be made flat to present a streamlined appearance.

The method of use of the probe of the present invention will now be described. The probe is placed in electrical connection with a standard electrochemical analyzer such as a D.G. Electro-Chem Analyzer (Model 1300, Series No. 900426-31) by means of a standard connector such as a mini-coaxial connector cable which is attached to the first and second leads of the probe. The mode switch of the analyzer is set down to a reference position, and the selector control to the millivolt position (inactivating most other controls). The power supply switch of the activator is turned on, and the probe tip is placed in sterile 0.5 molar NaCl solution (saline solution). A base line reading is then taken which will usually vary between 30-100 mV(+), reflecting the potential difference between the first and second electrodes in the probe, that is, silver versus silver/silverchloride in the saline solution.

The probe is now ready for insertion in a periodontal pocket of the patient. The probe is inserted so that it comes into contact with the periodontal sulcus fluid contained therein. The electrolytes within the fluid will cause an electrical potential between the first and second electrodes, the magnitude of which corresponds to the concentration of sulfide gases in the fluid. Typically, a clinically observable diseased or inflamed pocket should produce a readout on the electrochemical analyzer in the 500-700 mV(+) range, and more typically at the higher end of the range. Weak responses in the range of 160-200 mV may indicate subclinical disease activity not diagnosable by conventional means. Readings below this level may be borderline. Readings below the borderline (150 mV) down to baseline (typically 50-80 mV) indicate an absence of an active disease.

All of the periodontal pockets in a particular patient's mouth may be successively, and easily measured using the method of the present invention. After each successive pocket measurement, the probe tip is immersed in the sterile saline solution, until the reading on the analyzer drops to below a baseline value. To achieve this rapidly, the probe tip may be electronically depolarized within a few seconds, either by short circuiting, or by subjecting it to a negative voltage of approximately 10-25 millivolts. It is important that, between successive measurements, the probe be kept in the sterile solution until it "relaxes" to a baseline value of less than 100 mV; otherwise, it will not be possible to tell if the potential reading from the next pocket is actually caused by the presence of sulfides in the sulcus fluid or, rather, is just an artifact of the reading from the previous pocket. Electronic depolarization, alternatively, produces an "instantaneous relaxation" to the range of 50 mV.

In this manner, a succession of measurements may be taken for a particular patient. When the measurements for the particular patient have been performed, it is highly desirable that the probe be tested to see that it is correctly responsive to the presence of sulfides. To this end, the probe is first immersed in the 0.5 molar saline solution again and depolarized until the potential drops to an acceptable baseline value. The probe is then immersed momentarily in a $10^{-3}$ molar sulfide reference solution. The reading should immediately jump to over 600 mV(+), thus indicating that the probe is still sensitive to sulfides. The probe should be immediately removed from the sulfide reference solution and placed again in the saline solution and depolarized.

If this test procedure does not produce a 600 or greater mV(+) response, the silver chloride surface on the second electrode may have been compromised, either due to conversion to silver sulfide during probing, or possibly to poisoning of the probe surface by blood or pocket proteins. If so, it may be necessary to remeasure the patient's pockets with a fresh probe.

After the presterilized and hermetically packaged probe has been used on a single patient, it is intended to be discarded. The inventors have noted however that the probe will withstand conventional sterilization. Sterilization may be done in a number of ways, such as an ethylene oxide process. In the ethylene oxide process, the probes are first sealed in paper and plastic pockets, placed in wire baskets and then into a hermetically sealed chamber. A sealed cartridge of ethylene oxide is loaded into the chamber, and the probes are exposed to the gas for either four hours at 85° F. or, alternatively, for one hour at 145° F. Following this exposure the ethylene oxide gas is vented up a stack to the roof and the chamber is opened. The contents are transferred to another hermetic chamber for degassing; the items are flushed with air for eight hours at 145° F.

In a second, more conventional sterilization procedure, the probes are exposed to an atmosphere of 85% ethanol and a smaller percent of formaldehyde for 20 minutes inside a sterilization chamber which is held at approximately 220° F. It has been found that either of the described sterilization methods do not materially compromise the performance of the probe of the present invention. It is to be emphasized however that the probe is to be primarily regarded as a presterilized disposable.

EXAMPLES

Clinical trials of the probe of the present invention were performed on seven patients having a total of 56 tooth sites among them. The probes used were of two types, a tubular design (similar to that shown in FIG. 1), and a double wire design (similar to that shown in FIGS. 2-4). All the probes were sterilized prior to each trial. For each patient, the presence and extent of periodontal disease was assessed by conventional methods, such as inspection of the gingival margins and mechanical probing to determine the depth of the periodontal pockets. In each case, successive pocket readings were taken for each patient, the probe being immersed in a cup of sterile saline solution between each successive reading to return the data readout to the baseline level. After each trial, the probe used for that trial was tested in a reference sulfide solution as described above.

Patient No. 1 was a middle-aged man who, by prior examination, had both several diseased pockets and non-diseased pockets. A tubular probe was used for this trial. All of the diseased pockets gave probed responses of between 550-600 millivolts within a second or two of insertion of the probe. All of the non-diseased pockets gave readings in the (then) baseline level, between 200-300 millivolts. Note: These early research probes were not electronically depolarized; hence, the relatively high baseline values.

A double wire probe was used for the clinical trial on the second patient. Again, it had already been determined that the patient had both diseased and non-diseased pockets. This probe behaved similarly to the tubular probe except that, after a couple of pocket probings, the recovery to the baseline was slow. The potential did not go down very quickly from the 500-600 millivolt pocket reading to the baseline reading below 300 millivolts. The less satisfactory response of this probe may have been due to the fact that the exposed surface area of the electrodes was smaller than for the tubular probes, and the electrode surfaces may have become coated with proteins and blood which caused a sluggish response. Due to the sluggish response of this probe, examination of the patient was completed with a new probe. The more recent development of electronic depolarization techniques would have obviated the need for a second probe.

To help overcome the problem of the slow return to the baseline reading between successive pocket probings, a stronger 0.5 molar sterile saline solution was prepared for the rinsing process between successive probings to facilitate the return to the baseline reading. This saline solution was used on patient No. 3 and, again, the correlation between results obtained from probing and independent assessment of the presence or absence of disease in the pockets was very strong. In patient No. 3, the pockets did not have as much disease so the probe responses were not as dramatic. This indicates that the dual electrode probe of the present invention has the capacity to make qualitative assessments of various levels of disease. In no case, with the first three patients, was the delay in probe relaxation time any longer than 20–30 seconds, and that time period was encountered in only a small number of instances. Even so, electronic depolarization makes possible the nearly instantaneous recovery of a 50–100 mV baseline (1–2 seconds).

Patient No. 4 had been under treatment for periodontal disease. Hence, while this patient had several pockets, some of which were quite deep, they were fairly healthy. Significantly, the device of the present invention gave no responses significantly above the baseline level of 300 millivolts. This result correlated well with the absence of disease activity as separately assessed objectively by the dentist. In this case, a dual wire probe was used.

Patient No. 5 was a young female who had been on a course of antibiotics. Pocket probing response was minimal, indicating little or no disease. This correlated with the independent objective dental evaluation. The probe used on this patient was the same as the probe used on patient No. 2, and it had been sterilized in 80% ethanol and formaldehyde at 220° F.

In the case of patient No. 6, the first dual wire style probe did not work at all. It gave an essentially zero response in the saline at the start and, in the confirming test after the patient's session, it did not respond to the sulfide solution at all. An open circuit was suspected, but not confirmed. In any case, the malfunction was obvious at the very start before any probing. Another dual wire probe was used, which worked, but, since the patient had "tight," healthy gums, the response was minimally different from the baseline.

Patient No. 7 was a middle-aged man with a moderate degree of disease which had not been deemed serious in the prior, independent, evaluation. The probe readings went up to around 500 millivolts plus or minus about 20 millivolts, somewhat less than the maximum 600–700 millivolt characteristic of more severe disease.

These patient trials reveal that the dual electrode probe of the present invention, when used according to the method of the present invention, is capable of diagnosing both the presence and extent of periodontal disease and gingivitis in wide range of patients. For those patients who had both healthy and diseased pockets, the probe was able to make that selective determination. Significantly, in patients who had deep pockets where no disease was actively present, the probe correctly indicated the lack of active disease. Those patients having only moderately diseased pockets gave a moderate response in their probe readings. Finally, for patients having healthy gums and no pockets, the probe correctly indicated a healthy state. These trials show that the probe is capable of making accurate qualitative and quantitative assessments of the presence or absence, and extent of periodontal disease. Furthermore, the probe proved itself to be quick and easy to use in the clinical setting, and was quite reliable, especially considering that only prototypes and not fully engineered probes, were used for these trials.

Longer term longitudinal studies on a larger patient base are being initiated by the inventors in order to obtain statistically significant quantitative correlations between the probe's output and the severity of the disease.

We claim:

1. A method for diagnosing the presence and extent of disease activity in a periodontal pocket by measuring the concentration of sulfides therein, said method comprising the steps of:
   providing a dual electrode probe having a first uncoated silver electrode and a second, reference silver electrode including a silver chloride coating deposited thereon;
   providing a voltage indicator for generating a data readout reflective of the strength of the electrical potential between said first and second electrodes;
   making electrical connection between said first and second electrodes and said voltage indicator;
   positioning said probe within said periodontal pocket such that both said electrodes are in contact with periodontal sulcus fluid contained therein and said sulcus fluid bridges said electrode to cause a potential between said first and second electrodes, the magnitude of said potential corresponding to the concentration of sulfides in said fluid;
   reading the data readout provided by the voltage indicator and indicative of the concentration of sulfides within said pocket; and
   comparing the data readout with a predetermined standard to determine the presence and extent of periodontal disease.

2. A method of claim 1 further comprising the steps of placing said probe within a test saline solution and reading the data readout generated by the voltage indicator reflective of the potential difference between said first and second electrodes in the saline solution to establish a base line reading.

3. The method of claim 1 further comprising the step of electronically depolarizing the probe to achieve a nearly instantaneous baseline reading of less than 100 mV.

4. The method of claim 2 further comprising the step of testing the probe by placing it in an approximately 0.001 molar sulfide reference solution.

5. The method of claim 1 further comprising the step of sterilizing said probe prior to positioning the probe within the periodontal pocket.

6. A probe suitable for diagnosing the presence and extent of disease in a periodontal pocket containing sulcal fluid by measuring the concentration of sulfides in said fluid, said probe comprising:
   a housing having a length and diameter configured to be easily handled and manipulated in the mouth of a patient;
   a tip configured to probe a periodontal pocket, said tip being disposed at a first end of said housing;
   a pair of electrodes including a first uncoated silver electrode and a second, reference silver electrode having a silver chloride coating deposited thereon, each of said pair of electrodes having a surface portion at least partially exposed in said tip; and first and second electrical leads in communication with, respectively, said first and second electrodes;

said exposed surface portions of said electrodes generating an electrical potential difference between said electrodes as a function of the sulfide concentration of sulcal fluid when said tip is disposed within a periodontal pocket containing sulcal fluid, said fluid bridging said exposed surface portions of said electrodes.

7. The probe of claim 6 wherein said housing comprises a suitable length of double bore, bifilar polymeric tubing, and each of said first and second electrodes is formed of a suitable length of silver wire extending through a bore of said bifilar tubing.

8. The probe of claim 7 further comprising a potting material disposed in both bores of the bifilar tubing to surround and support said pair of silver wires.

9. The probe of claim 7 further comprising means for stiffening each bore of the bifilar polymeric tubing.

10. The probe of claim 6 wherein said housing further comprises a suitable length of metal tubing, said first electrode comprises a layer of silver plated onto portions of said tubing, and said second electrode comprises a chloride coated silver body disposed outside said housing.

11. The probe of claim 10 further comprising polymeric tubing enclosing and surrounding said metal housing, with a portion of said silver layer remaining exposed and uncovered by said polymeric tubing at the tip of said probe.

* * * * *